May 22, 1962 R. JACOBS Plant Pat. 2,147
STRAWBERRY PLANT
Filed April 1, 1960
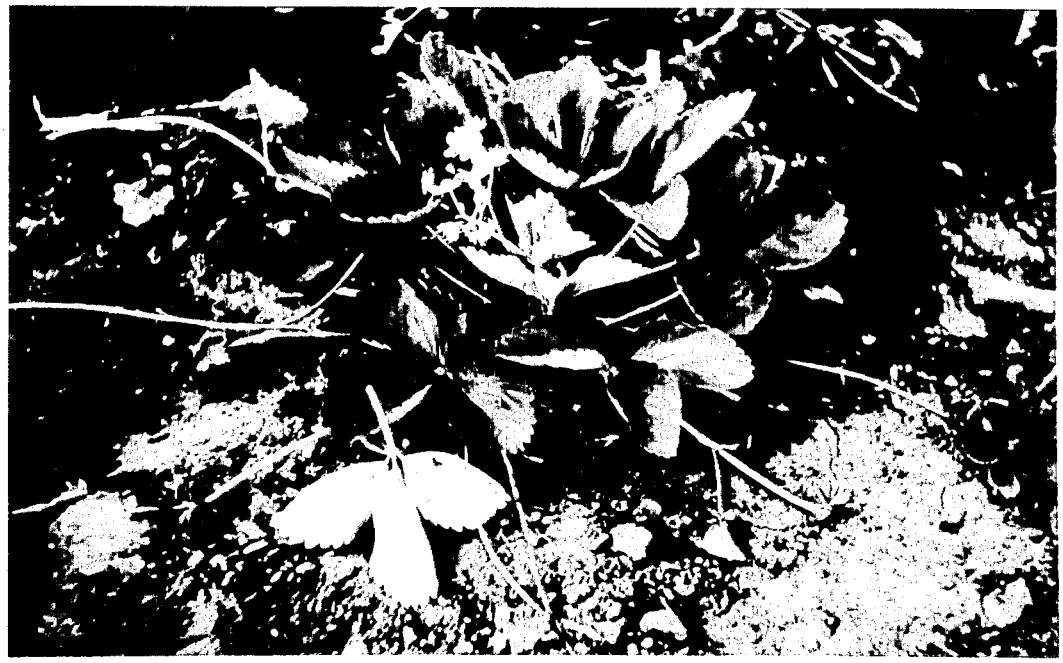
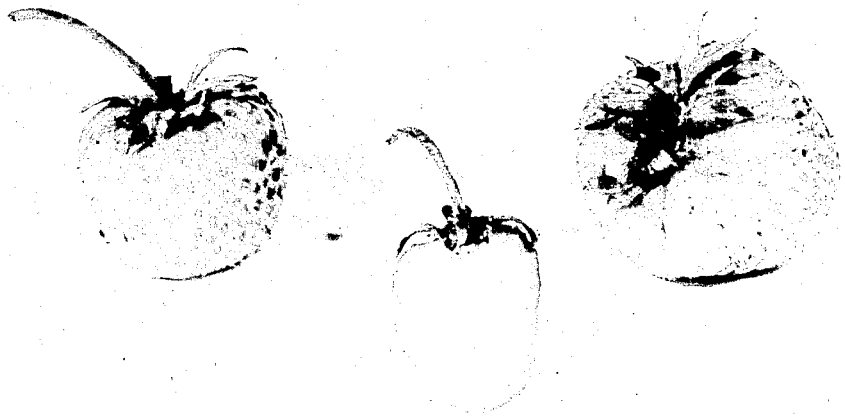
INVENTOR.
RUFUS JACOBS
BY John W. Adams
ATTORNEY United States Patent Office Plant Pat. 2,147
Patented May 22, 1962

2,147
STRAWBERRY PLANT

Rufus Jacobs, Bemidji, Minn., assignor to Farmer Seed & Nursery Company, Faribault, Minn., a corporation of Minnesota Filed Apr. 1, 1960, Ser. No. 19,435
1 Claim. (Cl. 47—62)

This invention relates to a new and distinct variety of strawberry plant.

The original plant was a chance seedling discovered by me in a row of seedlings of Montana Progressive variety (unpatented) on my farm in Port Hope Township, Beltrami County, Minnesota, several years ago. The new plant, therefore, is presumably a chance seedling of the Montana Progressive variety of strawberry plant.

I have asexually reproduced a large number of plants of this new variety on my farm in Port Hope Township, by means of transplanted runners, and the characteristics thereof appear to be permanent.

A berry, a leaf and a plant, of typical size and shape, are illustrated in the accompanying drawing, in which:

FIG. 1 is a perspective view showing three typical berries, one of which has been cut; and FIG. 2 is a perspective view showing a typical plant with blossoms and showing the under side of one leaf.

Referring now in more detail to my new variety of strawberry plant and the berries produced thereby, the plant and berries have the following distinctive characteristics which combine to distinguish them from the other known varieties.

The plant is extremely hardy. All plants have survived the severe winters of this area without any protective cover, and none of the plants have shown any trace of disease or insect infestation. The plants have roots much thicker and longer than Montana Progressive to give better drought resistance.

The plant is very prolific, producing approximately 15 to 20 large runners per plant. The first and second runner plants blossom and bear fruit the first year.

The first blossoms of my new variety of strawberry plant usually appear during the first week in May and the first crop of berries is ready for harvesting between June 10 and June 15. The last bearing for the first crop occurs approximately between July 5 and July 15. The second crop is ready for picking on about August 1, and the plant continues to yield berries until the first killing frost.

The blossoms are larger than those of other varieties generally grown in this area, including Montana Progressive. The leaves are also larger than the leaves of most other varieties and have a tendency to curl upwardly along the edges. The leaves are a brighter green and are slightly lighter in color than the leaves of the Montana Progressive and other varieties grown in this area.

The plants of my new variety are strong and thick and have a very vigorous habit of growth. The plants have no tendency to divide at the crown. The blossom stem holds the fruit well up from the soil, and each blossom stem generally produces 6 to 9 berries. The blossom stems frequently protrude upwardly through the leaves and hold the berries above the foliage.

The berries have a heavy, thick and generally round stem end with very high shoulders, and are uniformly tapered to a rounded wedge at the blossom end. The berry is thus generally similar in shape to that of the June Bearing Armore variety (unpatented) of strawberry plant.

The berries are larger than average, and are larger than Montana Progressive. The color of the berries is an extremely bright red tending toward a scarlet color. The berries are quite uniform in color. The flesh of the berry is also quite uniform in color, but there is a tendency toward a lighter zoning coloration at the heart. The heart of the berry is firm, but there is no hard core. Ripe berries are firm and have a very high sugar content. The taste is extremely sweet and acid free with a high strawberry flavor. Ripe berries remain in excellent firm condition during storage and shipping.

The plant is particularly characterized by its extreme hardiness and prolific production of hardy runner plants and by the large size of the leaves, blossoms and berries and the bright light green color of the leaves.

As a convenient summary, the following is a detailed description of this new variety of strawberry plant;

*Size.*—Very heavy root system. Roots very thick and long (much thicker and longer than the Montana Progressive variety).

*Crown size.*—The crown is generally ⅓ thicker, ⅓ longer and ⅓ heavier than the Montana Progressive variety.

*Leaves.*—Trifoliate leaves larger than average, which are slightly longer than the width thereof. The leaves are rounded at the outer edge and are generally uniformly serrated. Upper surfaces of leaves have a smooth shiny surface. Undersides of leaves are a considerably lighter green in color than the upper surfaces. Leaves are larger, brighter and lighter in color than leaves of the average variety, including Montana Progressive, and have a tendency to curl upwardly at the edges.

*Petiole.*—Generally the same length as Montana Progressive but heavier and hairier.

*Runners.*—Thick and very freely produced. Each mother plant produces 15 to 20 runners.

*Flower stems.*—Upright thick and partially exposed. Each stem generally produces 6 to 9 berries.

*Flower.*—Larger in size than most varieties and larger than flowers of the parent, Montana Progressive.

*Sex.*—Bisexual.

*Fruit stems.*—Sturdy and upright, holding fruit well off the ground and frequently supporting the berries above the plant foliage.

*Soil.*—Plants have been grown successfully in a large variety of soil type ranging from light sand to heavy clay.

*Disease resistance.*—Excellent resistance to leaf spot and leaf blight. Other strawberry plants, to-wit: Brilliant, Red Rich, Streamliner and 20th Century plants growing in the same or adjacent field areas showed a substantially higher incidence of these diseases.

*Frost resistance.*—All plants have survived −40° F. winter temperatures in the Bemidji area without any protective cover and with no snow cover.

*Fruit.*—Condition when described—prime.

*Size.*—Berries are larger than most varieties, including Montana Progressive.

*Surface contour.*—Generally quite regular.

*Shape.*—Round and generally symmetrical. The stem end has broad high shoulders which taper quite uniformly to a rounded wedge at the blossom end.

*Fruit stem.*—Heavy, upright and having many branch stems.

*Aspect.*—Generally scarlet color and glossy aspect.

*Seeds.*—Bright, moderately conspicuous and generally flush with berry surface.

*Core.*—Uniformly firm texture throughout. The berry has no hard core. The core is generally lighter in color than the rest of the flesh.

*Calyx.*—Raised slightly from top of berry surface; slight pubsecence; medium green color with reddish variegations.

*Flesh.*—Juicy, firm and generally similar in texture to Montana Progressive. The flesh has a higher sugar content than the parent, and, under storage, the flesh retains its fresh fruit qualities better than berries of the Montana Progressive variety.

The strawberry described above and the plant producing the same may vary in slight details, depending upon the climate and weather conditions and the soil conditions under which they are grown.

What is claimed is:

An everbearing strawberry plant substantially as herein shown and described characterized by the large number of hardy fruit producing runner plants, by the large bright green leaves and large blossoms, and by the large, firm generally rounded wedge-shaped berry bright red in color, with a lustrous and generally regular surface and a sweet, acid free flavor, and adapted to grow successfully and prolifically in a large variety of soil types under a variety of extreme weather conditions and particularly capable of surviving extremely cold winter weather.

No references cited.